United States Patent [19]
Juhasz

[11] Patent Number: 6,110,166
[45] Date of Patent: *Aug. 29, 2000

[54] METHOD FOR CORNEAL LASER SURGERY

[75] Inventor: Tibor Juhasz, Irvine, Calif.

[73] Assignee: Escalon Medical Corporation, Skillman, N.J.

[*] Notice: This patent issued on a continued prosecution application filed under 37 CFR 1.53(d), and is subject to the twenty year patent term provisions of 35 U.S.C. 154(a)(2).

[21] Appl. No.: 08/725,070

[22] Filed: Oct. 2, 1996

Related U.S. Application Data

[63] Continuation-in-part of application No. 08/407,508, Mar. 20, 1995, abandoned.

[51] Int. Cl.[7] ........................................ A61N 5/02
[52] U.S. Cl. ......................... 606/5; 606/3; 606/10; 606/13; 128/898
[58] Field of Search .................. 623/5; 606/4–6, 606/10–17; 128/898

[56] References Cited

U.S. PATENT DOCUMENTS

| | | |
|---|---|---|
| 3,769,963 | 11/1973 | Goldman . |
| 4,309,998 | 1/1982 | Aron nee Rosa . |
| 4,391,275 | 7/1983 | Frankhauser . |
| 4,538,608 | 9/1985 | L'Esperance, Jr. . |
| 4,580,559 | 4/1986 | L'Esperance . |
| 4,601,288 | 7/1986 | Myers . |
| 4,633,866 | 1/1987 | Peyman . |
| 4,655,913 | 4/1987 | L'Esperance, Jr. . |
| 4,669,466 | 6/1987 | L'Esperance . |
| 4,718,418 | 1/1988 | L'Esperance, Jr. . |
| 4,721,379 | 1/1988 | L'Esperance . |
| 4,732,148 | 3/1988 | L'Esperance . |
| 4,770,172 | 9/1988 | L'Esperance . |
| 4,773,414 | 9/1988 | L'Esperance, Jr. . |
| 4,842,599 | 6/1989 | Bronstein .................................. 623/5 |
| 4,907,586 | 3/1990 | Bille et al. ................................. 606/5 |
| 4,941,093 | 7/1990 | Marshali . |
| 4,988,348 | 1/1991 | Bille . |

OTHER PUBLICATIONS

Tadeusz Krawawicz, *Lamellar Corneal Stromectomy*, pp. 828–833.

John Marshall et al., Photoablative reprofiling of the cornea using an Excimer Laser; Photorefractive Keratectomy, Lasers in Ophtalmology, vol. 1, No. 1, pp. 21–48, 1986.

*Primary Examiner*—David M. Shay
*Attorney, Agent, or Firm*—Nydegger & Associates

[57] ABSTRACT

A method for corneal laser surgery includes directing the focal point of a focused laser beam at a start point in the stroma. The focal point is then moved along a predetermined path in the cornea to photodisrupt tissue and to create a flap or a plug of corneal tissue. Specifically, the flap or plug is crated with an undercut region that interlocks with an overlap region to restrain movement of the flap or plug in an anterior direction. Stromal tissue under the flap or plug can then be removed when the plug or flap is forceably lifted from the cornea. The flap or plug is subsequently replaced in its interlocking relationship with the remainder of the corneal tissue. The diminished stromal tissue reshapes the cornea in a manner which improves the vision of the patient.

15 Claims, 3 Drawing Sheets

METHOD FOR CORNEAL LASER SURGERY

This is a continuation-in-part patent application of application Ser. No. 08/407,508 filed on Mar. 20, 1995 now abondoned.

FIELD OF THE INVENTION

The present invention pertains generally to ophthalmic surgery which is useful for correcting vision deficiencies. More particularly, the present invention pertains to methods which surgically correct the vision of a patient by removing portions of the stroma to reshape the cornea. The present invention is particularly, but not exclusively useful as a method for using a laser beam to photodisrupt corneal tissue to achieve access to a predetermined volume of stromal tissue which needs to be removed to correct the vision of the patient.

BACKGROUND OF THE INVENTION

Vision impairment can occur for many reasons, and be the result of many causes. One, all too common, cause for vision impairment results from a defective condition of the eye which occurs when the refractive characteristics of the cornea do not cause parallel rays of light to focus on the retina. When the eye is at rest, and the rays of light focus in front of the retina, the condition is known as myopia (i.e. near-sightedness). On the other hand, when the rays of light focus behind the retina, the condition is known as hypermetropia or hyperopia (i.e. farsightedness). Both myopic and hyperopic conditions result in varying degrees of vision impairment and, as is well known, in most cases the conditions are correctable.

Spectacles or eyeglasses are commonly used to correct myopic or hyperopic conditions. For various reasons, however, many persons who suffer with these conditions prefer not to wear eyeglasses. Fortunately for these individuals, it is known that surgical procedures can be employed which will reshape the cornea in ways that are effective in changing its refractive characteristics. For example, U.S. Pat. No. 4,665,913 which issued to L'Esperance for an invention entitled "Method for Ophthalmological Surgery", and U.S. Pat. No. 4,669,466 which issued to L'Esperance for an invention entitled "Method and Apparatus for Analysis and correction of Abnormal Refractive Errors of the Eye" both disclose a laser system which photoablates corneal tissue from the anterior surface of the eye. In a different manner, U.S. Pat. No. 4,988,348 which issued to Bille for an invention entitled "Method for Reshaping the Cornea", and which is assigned to the same assignee as the present invention, discloses a procedure whereby corneal tissue is first removed to correct vision, and then the newly created surface is smoothed.

Rather than remove and reshape portions of the anterior portion of the eye to correct refractive defects, some procedures for reshaping the cornea have suggested intrastromal photoablation for removal of only stromal tissue. As an example of such a procedure, U.S. Pat. No. 4,907,586, which issued to Bille et al. for an invention entitled "Method for Reshaping the Eye" discloses an intrastromal photodisruption technique for reshaping the cornea. Another example of a procedure which is intended to essentially remove only stromal tissue is the so-called "flap and zap" procedure. For this procedure, an anterior portion of the cornea is removed and a portion of the exposed stroma is then photoablated. The previously removed anterior portion of the cornea is then repositioned on the cornea to cover the photodisruption. This procedure, like the procedure disclosed in Bille et al. '586, has as its objective the removal of only stromal tissue with the consequent preservation of anterior corneal tissue. A significant downside for the "flap and zap" procedure, however, is the possibility that the previously removed anterior portion of the cornea may again become detached. While the intrastromal procedure disclosed by Bille et al. does not lead to this detachment problem it can, in some cases, require extensive laser photodisruption and be time consuming.

In one aspect, it is appreciated by the present invention that the "flap and zap" procedure can be made more effective and efficient if the "flap" that is created can somehow be repositioned in an interlocking relationship with the undisturbed corneal tissue. To accomplish this, the present invention recognizes that it would be desirable if, first, a "flap" with an interlockable configuration is created. The flap could then be lifted to expose the corneal tissue that is to be removed and, next, after the desired amount of corneal tissue is removed, the flap could be repositioned and interlocked with undisturbed corneal tissue to hold the "flap" in place during the healing process.

The use of laser systems for ophthalmic surgical procedures, such as for other procedures contemplated for the present invention, is particularly appropriate due to the extreme precision required when corneal tissue is to be removed. Specifically, depending on the diameter and the general shape of the tissue volume to be removed, it is known that the removal of a layer of stromal tissue which is only approximately ten microns thick will result in a one diopter change. More practically, by way of example, the removal of a lens shaped volume of tissue which is four millimeters in diameter and approximately fifty microns thick at its center will result in a refractive correction of approximately four diopters. In almost all cases, for precise vision corrections which can stay within a one diopter accuracy, the surgical procedure employed must be capable of removing corneal tissue having a thickness which is accurate to within less than ten microns. Furthermore, this degree of accuracy applies for any refractive correction regardless of the total amount of correction required.

It happens that the correction of myopia requires removal of a differently shaped volume of corneal tissue than does the correction of hyperopia. Also, the limits of potential correction are different. Specifically, for a myopic correction it is known that a lentoid or lens shaped volume of stromal tissue needs to be removed. At the present time, myopic corrections of up to approximately thirty diopters can be reasonably expected. On the other hand, corrections of hyperopic conditions can be made up to only about fifteen diopters. Furthermore, for a hyperopic correction a generally doughnut shaped volume of stromal tissue, rather than a lens or lentoid shaped volume, needs to be removed.

In light of the above, it is an object of the present invention, to provide a method for corneal laser surgery which corrects the refractive characteristics of the cornea by removing only stromal tissue with minimal photodisruption of the tissue. Another object of the present invention is to provide a method for corneal laser surgery which essentially maintains the structural integrity of corneal tissue. Still another object of the present invention is to provide a method for corneal laser surgery which can be accomplished with a high level of precision when cutting corneal tissue by photodisruption. Another object of the present invention is to provide a method for corneal laser surgery which creates an interlocking flap that can be lifted to remove a predetermined volume of tissue from the stroma and then repositioned in an interlocking relationship with undisturbed corneal tissue to hold the flap in place during subsequent healing. Yet another object of the present invention is to provide a method for corneal laser surgery which is relatively easy to practice and comparatively cost effective.

SUMMARY OF THE PREFERRED EMBODIMENTS

In accordance with the present invention, a method for corneal laser surgery includes the step of first determining a volume of stromal tissue which needs to be removed in order to correct the vision of the patient. This volume of stromal tissue which is to be removed is formed as a lentoid that is defined by an anterior surface and a posterior surface. Accordingly, these surfaces are situated relative to each other so that the lentoid shaped volume of tissue to be removed is positioned therebetween.

A pulsed laser beam is focused to position its focal point at a preselected start point on the posterior surface of the lentoid. The focal point is then moved over the posterior surface to photodisrupt tissue on this surface and separate the lentoid from surrounding tissue. The same process is repeated for the anterior surface and the result is that the lentoid of stromal tissue to be removed is completely surrounded by photodisrupted tissue and thereby free of attachments to surrounding tissue.

In one embodiment of the present invention, looking at the eye in the direction from anterior to posterior, the posterior surface is shaped as a concave plate and the anterior surface is shaped as a convex plate. The removal of the resultant lens shaped tissue lentoid or disc is specifically intended to correct myopia. For the particular embodiment of the present invention wherein the correction of myopia is the desired result, it will be appreciated that the anterior surface or the posterior surface, or both, can be substantially flat. Also, the concave posterior surface could be modified to be a convex surface and thus have a curved surface which is similar to the anterior surface. On the other hand, in another embodiment of the present invention, the posterior surface is shaped as a concave annular surface and the anterior surface is shaped as a convex annular surface. In this instance the stromal tissue to be removed is a ring shaped or doughnut shaped volume which is specifically intended to correct hyperopia.

Regardless whether the volume is lens shaped or ring shaped, the method of the present invention also contemplates the creation of a channel through the stroma which provides for extracorporeal access to the encapsulated portion of the stroma. The encapsulated portion of the stroma can then be accessed, gripped, and removed or retrieved from the stroma through the channel. As intended for the present invention, with the removal of the lentoid volume of stromal tissue, the cornea is appropriately reshaped to correct the particular vision defect of the patient.

As intended for the present invention, the laser system to be used for accomplishing the methods will incorporate a beam of sequential laser pulses. Further, it is contemplated that the duration of laser pulses in the beam will be in the nanosecond, picosecond or femtosecond ranges.

For an alternative method of the present invention, the volume of tissue to be removed is as determined above. For this case, however, a flap is created which can be lifted from the cornea to provide for access to the tissue volume that is to be removed. Specifically, the flap is created as a layer of tissue having one surface which is a portion of the anterior surface of the cornea, and having an opposite surface therefrom which can either be a portion of the posterior surface of the cornea or a surface that is fashioned and cut from the stroma of the cornea. Further, this layer of tissue can be hinged to thereby allow rotation of the flap about the hinge, or it can be formed as an unhinged plug which can be entirely removed from the cornea and subsequently replaced. In either case the layer (regardless whether it be a flap or a plug), is created and formed with an undercut region which restrains its movement in an anterior direction.

BRIEF DESCRIPTION OF THE DRAWINGS

The novel features of this invention, as well as the invention itself, both as to its structure and its operation will be best understood from the accompanying drawings, taken in conjunction with the accompanying description, in which similar reference characters refer to similar parts, and in which.

DESCRIPTION OF THE PREFERRED EMBODIMENT

Figure 1:
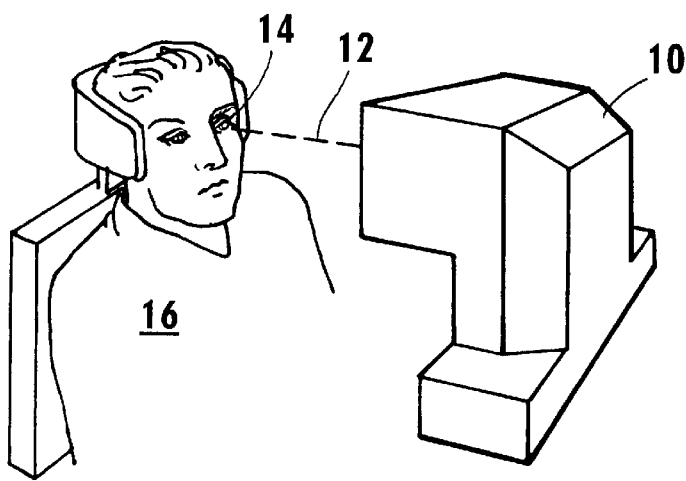
FIG. 1 is a perspective view of a patient being treated with the method of the present invention.

Referring initially to FIG. 1, an apparatus 10 for generating a laser beam 12 is shown. Specifically, the laser beam 12 is shown being directed onto an eye 14 of a patient 16.

For purposes of the present invention, the apparatus 10 is capable of generating a pulsed laser beam 12 having physical characteristics similar to those of the laser beams generated by a laser system as disclosed and claimed in U.S. Pat. No. 4,764,930, which is also assigned to the assignee of the present invention. Furthermore, the present invention contemplates the use of a pulsed laser beam 12 which has pulses with durations as long as a few nanoseconds or as short as only a few femtoseconds.

Figure 2:
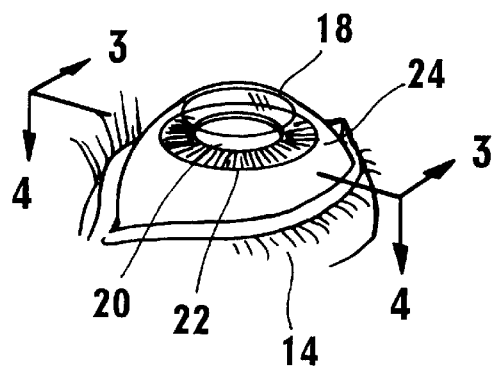
FIG. 2 is a perspective view of an eye.

FIG. 2 shows the anatomical structure of eye 14 and, specifically, that the cornea 18 is anterior to the pupil 20, the iris 22, and the sclera 24. Additionally, FIG. 2 indicates that the optical axis 26 of eye 14 passes through the cornea 18. Consequently, the tissue of cornea 18 is transparent to visible light.

Figure 3:
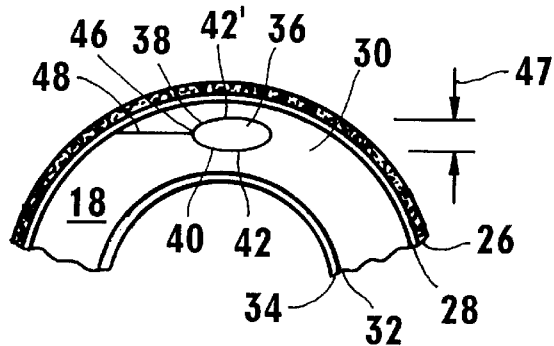
FIG. 3 is a cross sectional view of the cornea of the eye as seen along the line 3—3 in FIG. 2 showing a representative portion of stromal tissue to be removed for the correction of myopia.

In FIG. 3 it can be seen that the cornea 18 includes five anatomically definable layers of tissue. Going in a direction from anterior to posterior in FIG. 3, the tissue layers of the cornea are: epithelium 26, Bowman's membrane 28, stroma 30, Decemet's membrane 32 and endothelium 34. Of these, the stroma 30 is of most importance for the present invention as it contains the only tissue which is to be removed for correction of the patient's vision.

As indicated above, the correction of a myopic condition can be accomplished by the removal of a predetermined volume of stromal tissue. As also indicated above, the particular volume of stromal tissue to be removed for the correction of myopia will depend on the amount of correction required and will be a lens or lentoid shaped volume. Such a lentoid volume 36 is shown in cross section in FIGS. 3 and 3A. As shown, it is to also be appreciated that the lentoid volume 36 will be defined by an anterior surface 38 and a posterior surface 40. Together, the anterior surface 38 and the posterior surface 40 will completely enclose or encapsulate the lentoid volume 36 of stromal tissue 30 which is to be removed. To obtain the lens shape of the lentoid volume 36 it will be understood and further appreciated that, when considering lentoid volume 36 in a direction from anterior to posterior, the anterior surface 38 may be convex in shape and the posterior surface 40 may be concave in its shape.

Figure 3A:
FIG. 3A is a cross-sectional view of a lentoid having a convex anterior surface and a concave posterior surface.
Figure 3B:
FIG. 3B is a cross-sectional view of a lentoid having a convex anterior surface and a concave posterior surface which are separated by a contiguous flat annular surface therebetween.
Figure 3C:
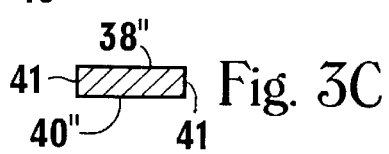
FIG. 3C is a cross-sectional view of a lentoid having a flat anterior surface and a flat posterior surface which are separated by a contiguous flat annular surface therebetween.

It is to be appreciated that the actual shape for lentoid 36 may vary according to the needs and desires of the physician. For example, several possible shapes for lentoid 36 are shown in FIGS. 3A, 3B and 3C. Specifically, the lentoid 36 shown in FIG. 3A is as suggested above where the anterior surface 38 is convex and the posterior surface 40 is concave. FIG. 3B shows a variation from this shape wherein the anterior concave surface 38' is separated from the posterior concave surface 40' by a substantially flat annular surface 41. As shown, the flat annular surface 41 is contiguous with both the anterior surface 38' and the posterior surface 40'. FIG. 3C shows yet another variation for lentoid 36 wherein both the anterior surface 38" and the posterior surface 40" are flat. Again, the anterior surface 38" and the posterior surface 40" are separated by the contiguous flat annular surface 41.

Figure 4:
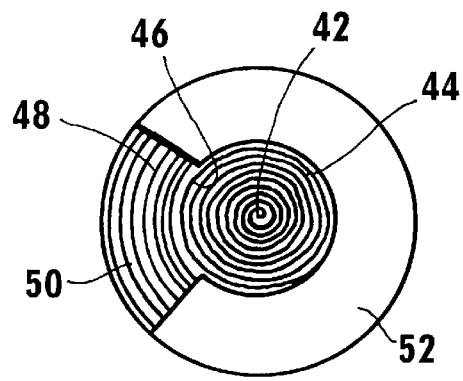
FIG. 4 is a plan view of the cornea of the eye as seen in the direction of the line 4—4 in FIG. 2 showing a representative path for movement of the laser beam focal point to prepare the portion of stromal tissue shown in FIG. 3 for removal from the cornea.

The creation of the anterior surface 38 and posterior surface 40 of lentoid volume 36 will, perhaps, be best appreciated with cross reference between FIG. 3 and FIG. 4. In FIG. 4, a predetermined start point 42 is shown, which is preferably on the posterior surface 40. The laser beam 12 is then focused initially on the predetermined start point 42 and, subsequently, the focal point of the laser beam 12 is moved according to computer programmed instructions along the spiral path 44. The spiral projection of the laser beam's focal point continues along spiral path 44 to create the concave posterior surface 40 until it reaches a point 46. Upon reaching the point 46 for the first time, the laser beam 12 is focused at a start point 42' on the anterior surface 38 of lentoid volume 36. The focal point of the laser beam 12 is then moved, again according to computer programmed instructions along a spiral path 42' to create the convex anterior surface 38 until the focal point again arrives at the point 46. With these actions the lentoid volume 36 is encapsulated and surrounded by photodisrupted tissue in the surfaces 38 and 40. For most applications the maximum distance 47 between the surfaces 38 and 40 will not exceed two hundred and fifty microns.

A channel 48 is next formed into the cornea 18 to provide for extracorporeal access to the lentoid volume 36. Specifically, the channel 48 will be created by the photodisruption of stromal tissue 30 in a manner similar to that used for the creation of anterior surface 38 and posterior surface 40. To accomplish this, a complete or a partial, or interrupted, spiral path 50 is followed by the focal point of laser beam 12. As can be appreciated by reference to FIG. 4, for a partial spiral path 50 the activation of laser beam 12 can be interrupted and turned off during the excursion of its focal point through an arc of predetermined magnitude. In FIG. 4 the arc in which the laser beam 12 is inactivated is shown as the space 52 and is estimated to be approximated two hundred and seventy degrees. On the other hand, the laser beam 12 is activated and the channel 48 is created over the remaining approximately ninety degrees of travel for the laser beam 12 focal point.

As implied above, it may be preferable to generate a complete spiral path 50, rather than the partial spiral path 50 shown in FIG. 4. To do this, laser beam 12 remains activated during photodisruption of stromal tissue during each complete 360° sweep of laser beam 12 along path 50. Thus, no space 52 is created and, instead, the spiral path 50 creates a layer of photodisrupted tissue. With this complete spiral path 50 pattern, it is subsequently possible to create an access channel 48 to the lentoid volume 36 from any direction. Additionally, the tissue of stroma 30 which is photodisrupted by each complete 360° sweep of laser beam 12 is symmetrically disposed around the lentoid volume 36. In some cases, this symmetrical disposition of photodisrupted tissue may be necessary in order to prevent a later development of irregular astigmatism.

Figure 5:
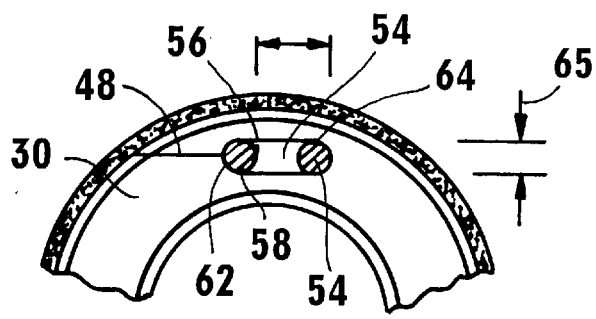
FIG. 5 is a cross sectional view of the cornea of the eye as seen along the line 3—3 in FIG. 2 showing a representative portion of stromal tissue to be removed for the correction of hyperopia.
Figure 6:
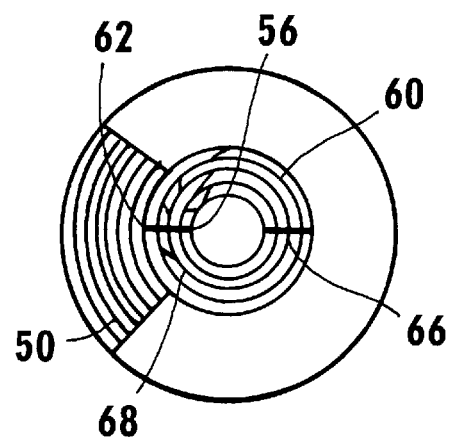
FIG. 6 is a plan view of the cornea of the eye as seen in the direction of the line 4—4 in FIG. 2 showing a representative path for movement of the laser beam focal point to prepare the portion of stromal tissue shown in FIG. 5 for removal from the cornea.

Turning now to FIG. 5, a procedure for the treatment of hyperopia is indicated. As shown, the annular tissue volume 54 to be removed from stroma 30 in this procedure has a slightly different shape than is required for the treatment of myopia. Specifically, the annular tissue volume 54 is annular shaped. One way to create this annular tissue volume 54 is to initially focus the laser beam 12 to a predetermined start point 56 on annular tissue volume 54. The posterior surface 58 of annular tissue volume 54 is then created by moving the focal point of laser beam 12 along a depth variable spiral path 60 until it reaches a point 62 to create a concave posterior surface 58. The focal point is then returned to the start point 56 and again moved along a spiral path 60' of variable depth to create the convex anterior surface 64 for annular tissue volume 54. Upon reaching the point 62 for the second time, a channel 48 can be created in substantially the same manner as disclosed above for the procedure to create a myopic condition.

In addition to the creation of the annular tissue volume 54, the procedure for creating the annular tissue volume 54 of stromal tissue 30 also requires that the annular tissue volume 54 be severed on a plane 66 which is between and generally perpendicular to the anterior surface 64 and the posterior surface 58. As will be appreciated by the skilled artisan, this severance of annular tissue volume 54 along plane 66 allows for removal of the annular tissue volume 54 through the channel 48. Additionally, if desired to further facilitate removal of the annular tissue volume 54 from cornea 18, the annular tissue volume 54 can also be severed along a plane 68 which is generally diametrically opposite from the plane 66 and which, like plane 66, is between and generally perpendicular to the surfaces 58 and 64.

Figure 7:
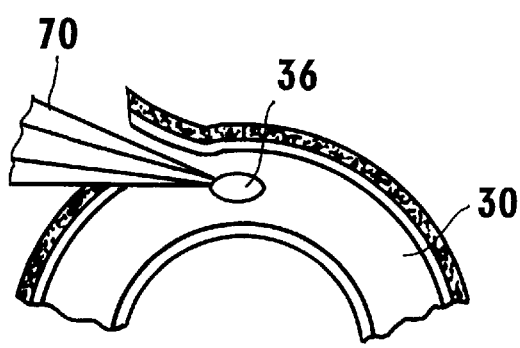
FIG. 7 is a cross sectional view of the cornea of the eye as seen along the line 3—3 in FIG. 2 showing the gripping of the portion of stromal tissue to be removed.
Figure 8:
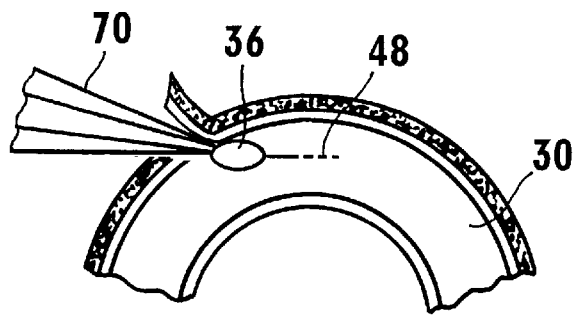
FIG. 8 is a cross sectional view of the cornea of the eye as seen along the line 3—3 in FIG. 2 showing the retrieval of the portion of stromal tissue to be removed.

Once the lentoid volume 36 or the annular tissue volume 54 of stromal tissue 30 has been created, as disclosed above, a device 70 can be inserted through channel 48, as shown in FIG. 7, to grip and then remove the particular volume from stroma 30, as shown in FIG. 8. For purposes of the present invention, the device 70 can be any instrument known in the pertinent art, such as a tweezers or a suction probe.

In another aspect of the present invention, the apparatus 10 can be used to create a section of corneal tissue which can be moved to expose, and thereby establish access to, the capsule volume 36 that is to be removed. For this particular procedure a layer 72 of corneal tissue is created which has an undercut region 74 that structurally interacts, or interlocks, with an intact overlap region 76 of the cornea. The idea here is to have the undercut region 74 interlock with the overlap region 76 so that the layer 72 does not unintentionally move in an anterior direction. For purposes of this disclosure, the anterior direction is to be considered as the general direction taken from the posterior surface 78 of cornea 18 (i.e. endothelium 34) toward the anterior surface 80 of cornea 18 (i.e. epithelium 26). Contrarily, the posterior direction is taken to be from the anterior surface 80 back toward the posterior surface 78.

For a description of how to create the layer 72, it is best to first identify a reference axis 82 from which distances and directions can be taken. For this purpose, consider the reference axis 82 to be oriented generally perpendicular to the anterior surface 80 of cornea 18, and to intersect the anterior surface 80 at a start point 84. The actual cutting the cornea 18 can be accomplished using any device well known in the art. For purposes of the present invention, however, it is preferred that corneal incisions be made using a laser light beam.

Figure 9:
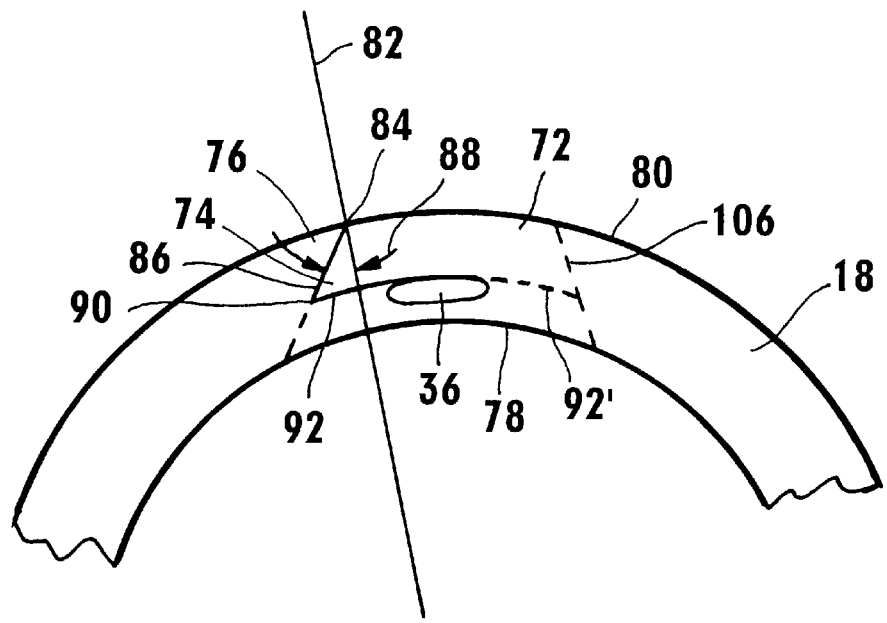
FIG. 9 is a cross sectional view of the cornea of an eye.

The creation of layer 72 begins by cutting the corneal tissue along a path 86 which is oriented at an angle 88 from the reference axis 82, and which extends from the start point 84 to a turn point 90. In practice, depending upon the particular desires of the operator, the path 86 can result in several different configurations for layer 72. One configuration, of course, is as shown in FIG. 9. For this particular configuration, the path 86 is essentially a straight line. In this case, the straight line is set at an acute angle 88 relative to the reference axis 82, and it extends from the start point 84 to the turn point 90. The undercut region 74 is then formed by cutting back toward the reference axis 82 along a path 92 which generally parallels the posterior surface 78. Again, depending on the desires of the operation, the path 86 can be something other than a straight line, so long as the start point 88 is generally located on the reference axis 82 and the turn point 90 is distanced from the axis 82 to create the undercut region 74.

Figure 10:
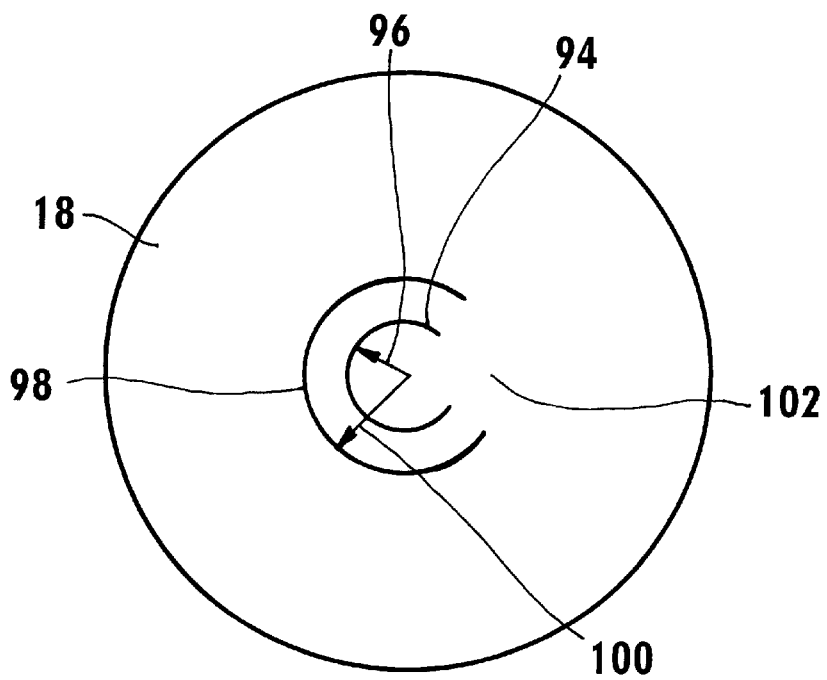
FIG. 10 is a plan view of the portion of the cornea shown in FIG. 9 looking at the anterior surface thereof in a posterior direction.

The implication from the above disclosure is that a plurality of different cuts, each along the different paths 86 and 92, need to be made in order to create the layer 72. Reference to FIG. 10, shows what the result of these several cuts might be. In FIG. 10 it will be seen that a plurality of start points 84 can be selected to establish a periphery 94. As shown, the periphery 94 is curvilinear and can be generally defined by a radius of curvature 96. Further, it can be appreciated by reference to FIG. 10 that a plurality of turn points 90 can be selected to establish a periphery 98. As shown, the periphery 98 is also curvilinear and can be generally defined by a radius of curvature 100. In order for the undercut region 74 to be established, it will be understood that the radius of curvature 100 must be greater than the radius of curvature 96. Additionally, as shown in FIG. 10, the peripheries 94 and 98 do not close. Thus, the a hinge area 102 is created and the layer 72 can be lifted as a flap in rotation about the hinge 102.

As an alternate configuration for the layer 72, it is to be appreciated that the layer 72 can be configured as a plug, rather than a flap. In this case, the peripheries 94 and 98 are closed paths, such as a circle. For this configuration there is no hinge 102. Referring back to FIG. 9, it will be seen that the plug configuration for layer 72 can be established by additional cutting. Specifically, this requires additional cutting on path 92 along the path continuation 92' and along a path 106 from the anterior surface 80 to the path 92' (both path continuation 92' and path 106 are shown by dashed line in FIG. 9).

Once the layer 72 has been created, either as a flap or a plug, the layer 72 can be mechanically lifted to expose an underlying capsule volume 36. As indicated above, the volume 36 can have many different sizes and shapes depending on the particular optical problem being confronted. In any case, once exposed, the volume 36 can be removed by procedures well known in the pertinent art. Importantly, after the volume 36 is removed, the layer 72 can be repositioned. When so repositioned, it is intended that the undercut region 74 will interact with overlap region 76 to restrain any further movement of the layer 72 in an anterior direction.

For some procedures it may be preferable to establish access all the way into eye. If so, the turn point 90 can be ignored and the path 86 be extended from the anterior surface 80 all the way to the posterior surface 78. Again, depending upon the extent of the cuts, and the respective resultant peripheries 94 and 98, the layer 72 can be created as either a flap or a plug.

While the particular Method for Corneal Laser Surgery as herein shown and disclosed in detail is fully capable of obtaining the objects and providing the advantages herein before stated, it is to be understood that it is merely illustrative of the presently preferred embodiments of the invention and that no limitations are intended to the details of the construction or design herein shown other than as defined in the appended claims.

What is claimed is:

1. A method for creating a replaceable layer of living corneal tissue in a cornea having an anterior surface and a posterior surface which comprises the steps of:

identifying a first surface area having a first periphery on the anterior surface of the cornea;

identifying a second surface area having a second periphery, said second surface area being larger than said first surface area and being substantially parallel thereto; and cutting along a substantially straight line between said first periphery and said second periphery; and back cutting on said second surface to create an undercut region for said layer with a hinge between said layer and said cornea, said undercut region restraining movement of said layer in a direction toward the anterior surface of the cornea during subsequent healing between said layer and the cornea.

2. A method as recited in claim 1 wherein said second surface area is near the posterior surface of the cornea.

3. A method as recited in claim 1 wherein said cutting step is accomplished using a beam of laser light.

4. A method as recited in claim 1 wherein said second surface area is created using a beam of laser light.

5. A method for creating an interlocking layer of living corneal tissue in a cornea having an anterior surface and a posterior surface, the method which comprises the steps of:

establishing a reference axis, said reference axis intersecting the anterior surface of the cornea at a first point and being substantially normal to the anterior surface;

cutting through the cornea along a first path from said first point to a second point, said first path being oriented at an angle from said reference axis, said first path being substantially straight;

back cutting through the cornea along a second path from said second point to a third point, said second path intersecting said axis and being oriented substantially perpendicular thereto to create said layer; and repeating said establishing step, said cutting step, and said back cutting step as required to create an undercut region for said layer with a hinge between said layer and the cornea, said undercut region restraining movement of said layer in a direction toward the anterior surface of the cornea during healing between said layer and the cornea.

6. A method as recited in claim 5 wherein said back cutting step is accomplished before said cutting step.

7. A method as recited in claim 5 wherein said repeated first points establish a first periphery having a first radius of curvature, and wherein said repeated second points establish a second periphery having a second radius of curvature, and further wherein said second radius of curvature is greater than said first radius of curvature.

8. A method as recited in claim 5 wherein said angle of said first path from said reference axis is an acute angle in a range between approximately zero degrees and ninety degrees (0°–90°).

9. A method as recited in claim 5 wherein said cutting step is accomplished by using a beam of laser light.

10. A method for creating an interlocking layer of living corneal tissue in a cornea having an anterior surface and a posterior surface which comprises the steps of:

identifying an axis relative to the cornea, said axis being substantially perpendicular to the anterior surface of the cornea;

establishing a first periphery in the cornea, said first periphery having a first radius of curvature about a first point on said axis;

establishing a second periphery in the cornea, said second periphery having a second radius of curvature about a second point on said axis, said second radius of curvature being greater than said first radius of curvature;

cutting the cornea along a substantially straight line between the first periphery and the second periphery to create said layer with an undercut region and with a hinge between said layer and said cornea;

displacing said layer from the cornea; and repositioning said layer with the cornea to restrain movement of said layer with said undercut region in a direction toward the anterior surface of the cornea during healing between said layer and the cornea.

11. A method as recited in claim 10 wherein said first periphery is on the anterior surface of the cornea.

12. A method as recited in claim 10 wherein said second periphery is on the posterior surface of the cornea.

13. A method as recited in claim 10 wherein said second periphery is more posterior in the cornea than said first periphery.

14. A method as recited in claim 10 wherein said cutting step is accomplished by using a beam of laser light.

15. A method as recited in claim 10 wherein said first periphery is substantially a portion of a circle and said second periphery is substantially a portion of a circle.

* * * * *